(12) United States Patent
Moon et al.

(10) Patent No.: US 11,420,190 B2
(45) Date of Patent: Aug. 23, 2022

(54) PROCESS FOR PREPARING POROUS IRON OXIDE-ZIRCONIA COMPOSITE CATALYST, POROUS IRON OXIDE-ZIRCONIA COMPOSITE CATALYST PREPARED THEREBY, AND METHOD FOR PRODUCING ALCOHOL USING THE CATALYST

(71) Applicant: SOGANG UNIVERSITY RESEARCH FOUNDATION, Seoul (KR)

(72) Inventors: Jun Hyuk Moon, Seoul (KR); Jae Hyun Lee, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 325 days.

(21) Appl. No.: 16/728,659

(22) Filed: Dec. 27, 2019

(65) Prior Publication Data

US 2020/0129965 A1 Apr. 30, 2020

Related U.S. Application Data

(62) Division of application No. 16/134,424, filed on Sep. 18, 2018, now abandoned.

(30) Foreign Application Priority Data

Aug. 22, 2018 (KR) .................. 10-2018-0098264

(51) Int. Cl.
*B01J 23/745* (2006.01)
*B01J 21/06* (2006.01)
(Continued)

(52) U.S. Cl.
CPC .......... *B01J 23/745* (2013.01); *B01J 21/066* (2013.01); *B01J 23/002* (2013.01);
(Continued)

(58) Field of Classification Search
CPC ....... B01J 21/066; B01J 23/002; B01J 23/745
See application file for complete search history.

(56) References Cited

U.S. PATENT DOCUMENTS 5,786,294 A * 7/1998 Sachtler ................. B01J 37/033
502/223
9,387,464 B2 7/2016 Miura et al.
(Continued)

FOREIGN PATENT DOCUMENTS

KR 101779301 9/2011

OTHER PUBLICATIONS

Petkovich (Chapter 4—Colloidal Crystal Templating Approaches to Materials with Hierarchical Porosity in Hierachically Structured Porous Materials, From Nanoscience to Catalysis, Separation, Optics, Energy and Life Science, Edited by YAng et al, Wiley-VCH, Nov. 28, 2011).*

(Continued)

*Primary Examiner* — Jun Li
(74) *Attorney, Agent, or Firm* — Myers Bigel, P.A.

(57) ABSTRACT

The present invention relates to a porous iron oxide-zirconia composite catalyst, a preparation method thereof, and a method for producing alcohol using the same, and the iron oxide-zirconia composite catalyst having a porous structure may produce alcohol at low cost by carrying out an excellent methane reforming reaction even under room temperature and room pressure conditions through an electrochemical reaction.

6 Claims, 10 Drawing Sheets

(51) Int. Cl.
  *B01J 37/08* (2006.01)
  *B01J 35/10* (2006.01)
  *C07C 29/48* (2006.01)
  *B01J 37/00* (2006.01)
  *B01J 37/02* (2006.01)
  *B01J 23/00* (2006.01)

(52) U.S. Cl.
  CPC ....... *B01J 35/1009* (2013.01); *B01J 35/1014* (2013.01); *B01J 35/1019* (2013.01); *B01J 35/1023* (2013.01); *B01J 35/1066* (2013.01); *B01J 35/1071* (2013.01); *B01J 37/0018* (2013.01); *B01J 37/0201* (2013.01); *B01J 37/0236* (2013.01); *B01J 37/088* (2013.01); *C07C 29/48* (2013.01)

(56) References Cited

U.S. PATENT DOCUMENTS

2012/0259144 A1  10/2012  Stauffer
2015/0080211 A1*  3/2015  Miura .................... C01G 25/00
                                                    501/134
2015/0314274 A1*  11/2015  Shen ........................ B01J 23/40
                                                    502/343
2016/0361248 A1*  12/2016  Vidal .................... A61K 8/0279

OTHER PUBLICATIONS

Hammond et al. "Direct Catalytic Conversion of Methane to Methanol in an Aqueous Medium by using Copper-Promoted Fe-ZSM-5" Angew. Chem. Int. Ed. 51:5129-5133 (2012).

Xu et al. "Continuous selective oxidation of methane to methanol over Cu- and Fe- modified ZSM-5 catalysts in a flow reactor" Cardiff Catalysis Institute, Cardiff University, 25 pages (2016).

Hu et al. "A core-shell structured Fe2O3/ZrO2@ZrO2 nanomaterial with enhanced redox activity and stability for CO2 conversion" Journal of CO2 Utilization, 17:20-31 (2017).

Cho et al. "Highly Ordered Mesoporous Fe2O3-ZrO2 Bimetal Oxides for an Enhanced CO Hydrogenation Activity to Hydrocarbons with Their Structural Stability" ACS Catalysis, 7(9):5955-5964 (2017).

\* cited by examiner

PROCESS FOR PREPARING POROUS IRON OXIDE-ZIRCONIA COMPOSITE CATALYST, POROUS IRON OXIDE-ZIRCONIA COMPOSITE CATALYST PREPARED THEREBY, AND METHOD FOR PRODUCING ALCOHOL USING THE CATALYST

RELATED APPLICATIONS

This application is a divisional of U.S. patent application Ser. No. 16/134,424, filed Sep. 18, 2018, which claims priority to Korean Patent Application No. 10-2018-0098264, filed Aug. 22, 2018, the disclosure of which is incorporated herein by reference herein in its entirety.

FIELD

The present invention relates to a process for preparing porous iron oxide-zirconia composite catalyst, a porous iron oxide-zirconia composite catalyst prepared thereby, and a method for producing alcohol using the catalyst.

BACKGROUND

Methane, which is a main component of gas, has problems with transportation and storage unlike liquid petroleum resources due to physical properties, so that when the production site is far away from the market, the use thereof is limited. It is possible to increase the added value of the gas, of which the use is so limited and of which the value is low, by physical liquefaction (LNG) or chemical conversion.

In the chemical methane conversion method, an indirect conversion route via a syngas ($CO/H_2$) is used. In order to produce the syngas in the indirect conversion route, there are a reforming process, a Fischer-Tropsch (FT) synthesis process for producing olefin or a liquid hydrocarbon from the syngas, a process for synthesizing methanol from the syngas, a process for producing gasoline or olefin via methanol, and the like, and through these processes, almost all fuel and chemical products, which may be obtained from existing petroleum-based raw materials, may be obtained from methane.

In brief, the conversion process of methane goes through a two-step process including a dry reforming reaction that produces a syngas by a partial oxidation reaction of methane and a process for producing products from the syngas. The standard reaction enthalpy of the dry reforming reaction is 247 kJ/mol, and such a process requires a catalyst under high temperature conditions. Accordingly, most of the methane conversion catalyst studies have been conducted from the viewpoint of cost reduction of commercialized processes targeting the conversion of methane into a syngas at lower temperature.

However, the conversion into the syngas is inefficient because the conversion goes through CO as an intermediate. Accordingly, studies on directly converting methane into products have become gradually important. The direct conversion of methane directly produces products by a reaction of a partial oxidation of methane (hereinafter, referred to as POM) or by a reaction of an oxidative coupling of methane (hereinafter, referred to as OCM). Since the direct conversion of methane directly obtains products, the selectivity is an important point.

Between the reactions, the partial oxidation reaction is generally advantageous in obtaining a specific product because the partial oxidation reaction exhibits high selectivity toward the specific product as compared to the OCM reaction. For the direct conversion of methane, numerous studies on a reaction of obtaining methanol and formaldehyde have been conducted.

A study conducted by Ceri Hammond et al., accomplished a conversion of methane into methanol by using a Cu-ZSM-5 catalyst under NO conditions, but still requires high temperature conditions at 150° C. and exhibits low selectivity and a low yield.

A study conducted by Jun Xu et al., achieved methanol selectivity of 92% at low temperature by using a Cu- and Fe-improved ZSM-5 catalyst, but exhibited a very low methane conversion of 0.5%.

SUMMARY

Accordingly, a technical object of the present invention is to provide a process for preparing a porous iron oxide-zirconia composite catalyst, which can produce alcohols with low cost by oxidating methane in room temperature and pressure, a porous iron oxide-zirconia composite catalyst prepared thereof, and a method for producing alcohols using the catalyst.

To solve the above-mentioned technical issues, an aspect of the present invention provides a process for preparing a porous iron oxide-zirconia composite catalyst including the following steps:

impregnating a polymer template mold with a precursor mixture of iron oxide precursor and a zirconia precursor;

drying the polymer template mold impregnated with the precursor mixture; and sintering the dried polymer template mold.

Another aspect of the present invention provides a porous iron oxide-zirconia composite catalyst prepared by the above-mentioned process and the average pore size thereof is 50 to 100 nm.

Still another aspect of the present invention relates to a method for producing alcohol, the method including: bringing a porous iron oxide-zirconia composite catalyst into contact with methane.

According to an aspect of the present invention, by preparing a porous iron oxide-zirconia composite catalyst with improved reactivity by structure control and with excellent selectivity, alcohols may be produced at low cost by oxidating methane at room temperature and pressure.

DETAILED DESCRIPTION

Figure 1A:
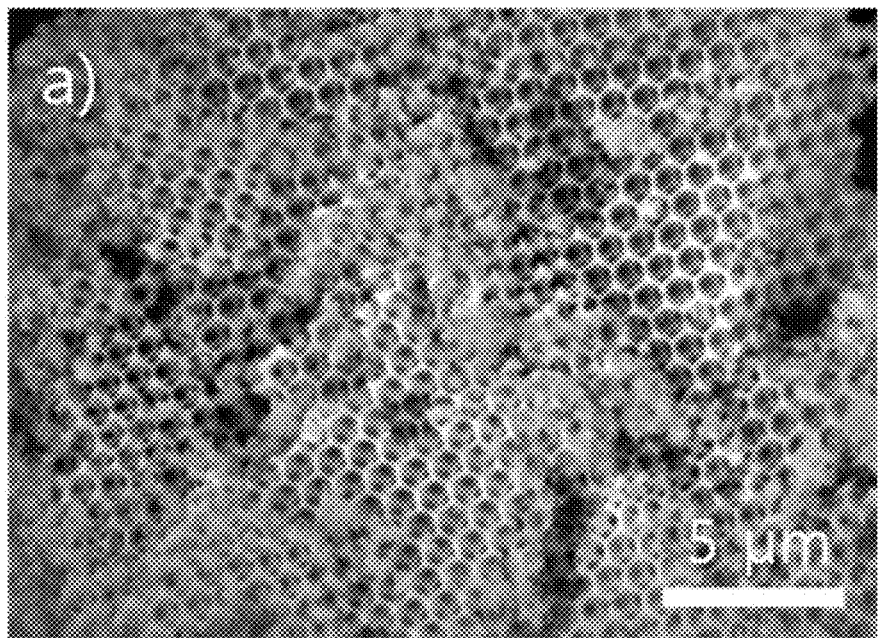
FIG. 1A is a high-magnification electron microscope image (magnification: ×5,000) of a porous iron oxide-zirconia composite catalyst produced according to the exemplary embodiment 1 of the present invention.
Figure 1B:
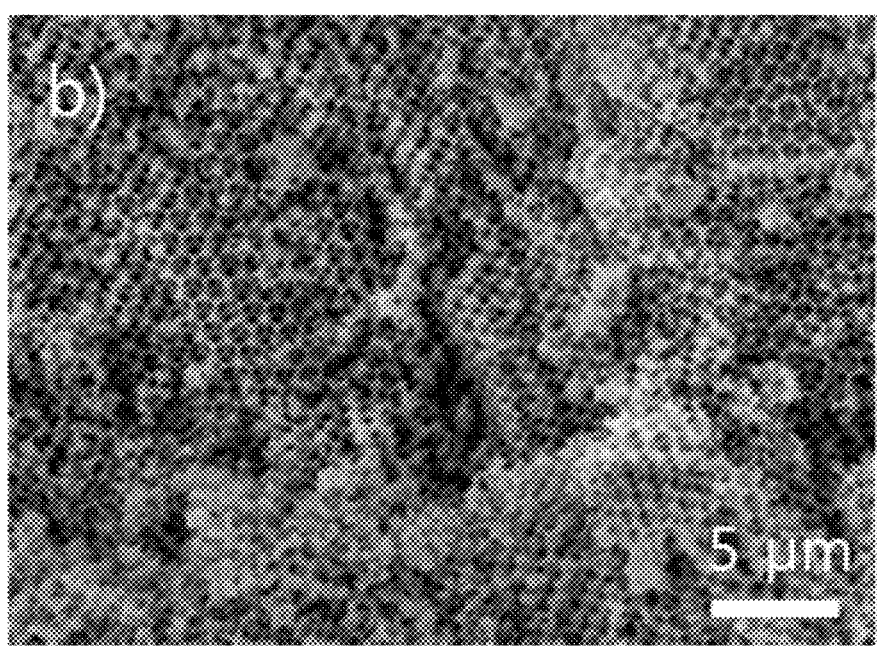
FIG. 1B is a high-magnification electron microscope image (magnification: ×3,500) of a porous iron oxide-zirconia composite catalyst produced according to the exemplary embodiment 2 of the present invention.
Figure 1C:
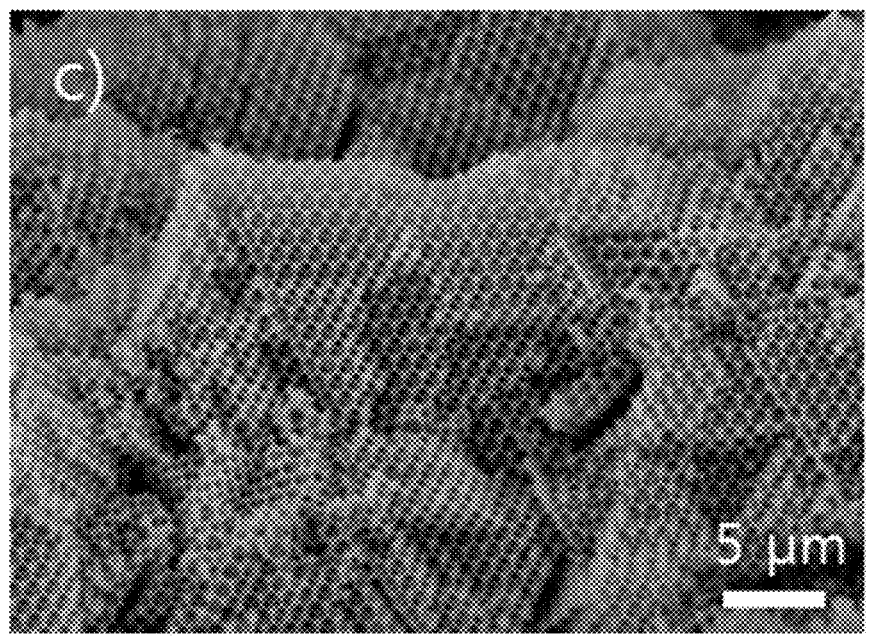
FIG. 1C is a high-magnification electron microscope image (magnification: ×3,000) of a porous iron oxide-zirconia composite catalyst produced according to the exemplary embodiment 3 of the present invention.
Figure 1D:
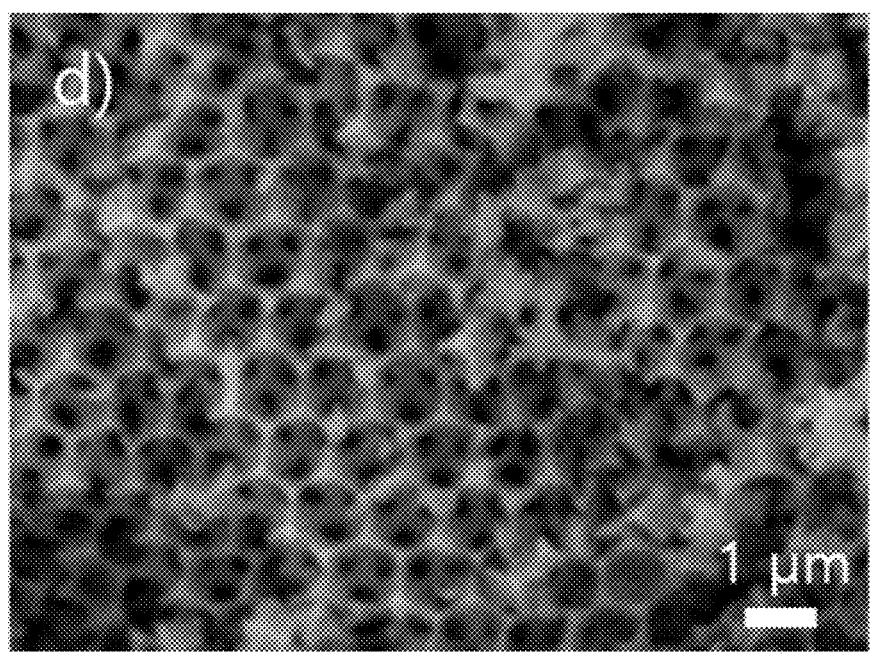
FIG. 1D is a high-magnification electron microscope image (magnification: ×10,000) of a porous iron oxide-zirconia composite catalyst produced according to the exemplary embodiment 1 of the present invention.
Figure 1E:
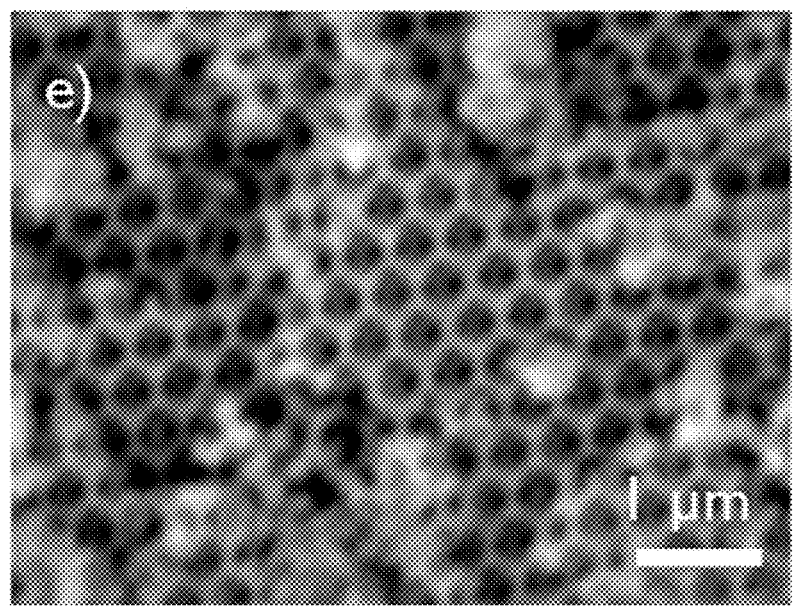
FIG. 1E is a high-magnification electron microscope image (magnification: ×3,000) of a porous iron oxide-zirconia composite catalyst produced according to the exemplary embodiment 4 of the present invention.

Hereinafter, the process for preparing the porous iron oxide-zirconia composite catalyst, the porous iron oxide-zirconia composite catalyst prepared thereby, and method for producing alcohol using the catalyst, according to an aspect of the present invention, will be described in more detail.

The process for preparing a porous iron oxide-zirconia composite catalyst according to an aspect of the present invention includes impregnating polymer template mold with a precursor mixture of iron oxide precursor and a zirconia precursor; drying the polymer template mold impregnated with the precursor mixture; and sintering the dried polymer template mold.

The process for producing the porous iron oxide-zirconia composite catalyst according to an aspect of the present invention may produce a catalyst having uniform pores with a simple method.

The above-mentioned iron oxide precursor may be one or more selected from the group consisting of iron (III) nitrate, iron (III) chlorate, and iron (III) sulfate.

The zirconia precursor may be one or more selected from the group consisting of zirconium oxynitrate, zirconium nitrate, and zirconium sulfate.

The iron oxide precursor and the zirconia precursor may be injected at a molar ratio of 8:1 to 2:1, for example, 8:1. When using the iron oxide precursor and the zirconia precursor within the above range of the ratio, the composite catalyst may be advantageous in methane oxidation reaction as an electrochemical catalyst, since the composite catalyst has high electroconductivity.

The iron oxide precursor and the zirconia precursor may be used in solution state using water, methanol or ethanol as a solvent The polymer template mold may include a spherical polymer arranged in a face centered cubic (fcc) structure.

The polymer template mold may be prepared by a method including emulsion polymerization of monomers and subsequent drying. Specifically, a spherical polymer template mold arranged in a face centered cubic (fcc) structure may be obtained by emulsion-polymerizing a reaction mixture including monomers, an initiator and an organic solvent, and centrifuging the emulsion including the polymer manufactured, followed by drying the product.

Being arranged in a fcc structure means that colloidal particles confined to fine liquid drops approach to each other due to the action of the capillary force generated by contraction phenomenon according to evaporation of the solvent, and finally form a self-assembly. Especially, being arranged in a fcc structure means that when a colloidal solution, the particle sizes thereof are uniform, self-assembled in a fcc structure, the colloidal solution may be used as a template mold for manufacturing an arranged three dimensional structure since the colloidal particles are assembled in a periodically arranged shape.

When centrifuging the emulsion, the centrifuging may be carried out at 6000 to 10000 rpm for 5 minutes to 30 minutes, but may be carried out at different condition according to the manufactured polymer. The emulsion may not include emulsifier when polymerized.

The polymer template mold may be a polymer template mold including one or more polymers selected from the group consisting of poly(methyl methacrylate)[PMMA], poly(butyl methacrylate)[PBMA], poly(methyl methacrylate)(butyl methacrylate), poly(hydroxyethyl methacrylate)[PHEMA], and polystyrene. A polymer template mold may include, for example, polystyrene.

impregnating a polymer template mold with the precursor mixture of the iron oxide precursor and the zirconia precursor may be carried out by adding distilled water to the iron oxide precursor and the zirconia precursor, and immersing the polymer template mold therein.

The polymer template mold may be impregnated with the mixture of the precursors at room temperature for 10 to 60 minutes, for example, for 30 minutes.

Next, the polymer template mold impregnated with the precursor mixture is taken out of the mixture and dried. The polymer template mold may be dried at 50° C. to 80° C., for example, at 65° C. for 10 hours to 15 hours, for example, for 12 hours, but are not limited thereto.

Next, the porous iron oxide-zirconia composite may be obtained by sintering the dried polymer template mold to carbonize the polymer template mold.

The dried polymer template mold may be sintered at 500° C. to 1300° C., for example at 700° C. to 1100° C., for example at 900° C., for 2 to 6 hours, 3 to 5 hours, for example for 4 hours.

The porous iron oxide-zirconia composite catalyst having uniform pores may be obtained by the above-mentioned method.

In another aspect of the present invention, the porous iron oxide-zirconia composite catalyst may be manufactured by the above-mentioned method, and have the average pore size of 50 nm to 900 nm. For example, the average pore size may be 55 nm to 900 nm, 60 nm to 900 nm, 65 nm to 900 nm, 70 nm to 900 nm, 50 nm to 800 nm, 55 nm to 800 nm, 60 nm to 800 nm, 65 nm to 800 nm, 70 nm to 800 nm, 50 nm to 700 nm, 55 nm to 700 nm, 60 nm to 700 nm, 65 nm to 700 nm, 70 nm to 700 nm, 50 nm to 600 nm, 55 nm to 600 nm, 60 nm to 600 nm, 65 nm to 600 nm, 70 nm to 600 nm, 50 nm to 500 nm, 55 nm to 500 nm, 60 nm to 500 nm, 65 nm to 500 nm, 70 nm to 500 nm, for example, 400 nm, but not limited thereto.

The porous iron oxide-zirconia composite catalyst may have a specific surface area of 1 to 1,000 $m^2/g$, 10 to 1,000 $m^2/g$, 20 to 1,000 $m^2/g$, 30 to 1,000 $m^2/g$, 40 to 1,000 $m^2/g$, 50 to 1,000 $m^2/g$, 60 to 1,000 $m^2/g$, 70 to 1,000 $m^2/g$, 1 to 800 $m^2/g$, 10 to 800 $m^2/g$, 20 to 800 $m^2/g$, 30 to 800 $m^2/g$, 40 to 800 $m^2/g$, 50 to 800 $m^2/g$, 60 to 800 $m^2/g$, 70 to 800 $m^2/g$, 1 to 600 $m^2/g$, 10 to 600 $m^2/g$, 20 to 600 $m^2/g$, 30 to 600 $m^2/g$, 40 to 600 $m^2/g$, 50 to 600 $m^2/g$, 60 to 600 $m^2/g$, 70 to 600 $m^2/g$, 1 to 400 $m^2/g$, 10 to 400 $m^2/g$, 20 to 400 $m^2/g$, 30 to 400 $m^2/g$, 40 to 400 $m^2/g$, 50 to 400 $m^2/g$, 60 to 400 $m^2/g$, 70 to 400 $m^2/g$, 1 to 200 $m^2/g$, 10 to 200 $m^2/g$, 20 to 200 $m^2/g$, 30 to 200 $m^2/g$, 40 to 200 $m^2/g$, 50 to 200 $m^2/g$, 60 to 200 $m^2/g$, 70 to 200 $m^2/g$, 1 to 100 $m^2/g$, 10 to 100 $m^2/g$, 20 to 100 $m^2/g$, 30 to 100 $m^2/g$, 40 to 100 $m^2/g$, 50 to 100 $m^2/g$, 60 to 100 $m^2/g$ or 70 to 100 $m^2/g$, for example, 70 $m^2/g$.

The porous iron oxide-zirconia composite catalyst may have a porosity of 1 to 99%, 1 to 90%, 1 to 80%, 10 to 99%, 10 to 90%, 10 to 80%, 20 to 99%, 20 to 90%, 20 to 80%, 30 to 99%, 30 to 90%, 30 to 80%, 40 to 99%, 40 to 90%, 40 to 80%, 50 to 99%, 50 to 90%, 50 to 80%, 60 to 99%, 60 to 90%, 60 to 80%, for example, 70%.

In the porous iron oxide-zirconia composite catalyst, the average pore size and the porosity may be controlled according to the particle size of a polymer template mold.

The composite catalyst may have a molar ratio of iron oxide to zirconia of 9.9:0.1 to 4.0:6.0, 9.0:1.0 to 4.0:6.0, for example, 9.0:1.0, 8.0:2.0, 7.0:3.0 or 6.0:4.0, but the molar ratio is not limited thereto.

In the porous iron oxide-zirconia composite catalyst, zirconia may be present in the form of tetragonal phase.

The methane oxidation reaction by the electrochemical reaction goes through a process in which $CO_3^{2-}$ is absorbed onto zirconia, and methane activated by iron oxide is oxidized by $O^{2-}$ transferred from the surface of zirconia. Accordingly, it is ideal that iron oxide and zirconia elements are present in a uniformly dispersed state.

Since the tetragonal phase zirconia has Lewis acid positions which are 3.5 times more than those of the monoclinic phase zirconia, the tetragonal phase zirconia has a structure which is advantageous in an electrochemical methane oxidation reaction in carbonate ion absorption characteristics.

Iron is known to have an excellent performance in activating the C—H bond of methane. Under high temperature conditions, it is possible to oxidize methane while providing oxygen ions along with the activation of methane. However, it is difficult to break the C—H bond of methane and provide oxygen ions under room temperature conditions. $CO_3^{2-}$ in an alkaline solution provides oxygen to iron oxide to form Ferryl 0, and $CH_4$ is oxidized by Ferryl 0 to form methanol.

Zirconia is known to adsorb carbonate well. However, zirconia has a bonding interval of 5 eV, so that electrons cannot be transferred, and an electrochemical reaction cannot occur when zirconia is used alone. Accordingly, when zirconia is used alone, it is difficult for a reaction of oxidizing methane to occur because it is difficult for a reaction of electrochemically reducing $CO_3^{2-}$ to $CO_2$ to occur. Therefore, in a methane oxidation reaction at room temperature, two elements of iron oxide which serves to activate the C—H bond of methane and zirconia which helps oxidation are essential.

Still another aspect of the present invention relates to a method for producing alcohol, the method including: bringing a porous iron oxide-zirconia composite catalyst into contact with methane.

The method for producing alcohol may include allowing the porous iron oxide-zirconia composite catalyst according to the present invention to react with a solution including methane.

The production method may be carried out at 5 to 40° C., 5 to 35° C., 5 to 30° C., 5 to 25° C., 5 to 20° C., 10 to 40° C., 10 to 35° C., 10 to 30° C., 10 to 25° C., 10 to 20° C., 15 to 40° C., 15 to 35° C., 15 to 30° C., 15 to 25° C., 15 to 20° C., 20 to 40° C., 20 to 35° C., 20 to 30° C. or 20 to 25° C., and may be carried out, for example, at 20° C., and the production method may be carried out within a temperature range which does not impair a reactor and electrodes, and the higher the temperature is, the more advantageous the reaction is, but there may occur a problem in that the methane saturation degree deteriorates.

The production method may be carried out at a pressure of 1 to 20 bar, 1 to 15 bar, 1 to 10 bar, 1 to 5 bar, 1 to 3 bar, 1 to 2 bar or 1 to 1.5 bar, and may be carried out at a pressure of, for example, 1 bar. As the pressure is increased within a range which does not impair a reactor, the methane saturation degree in the solution is increased, which is advantageous in the reaction, but the production method may be carried out at room pressure in consideration of economic feasibility with respect to the reaction.

The catalyst may be used for producing alcohol, formaldehyde, acetaldehyde, or acetone, for example, for producing alcohol, but not limited thereto.

The alcohol may be methanol, 1-propanol, 2-propanol, or ethanol, but is not limited thereto.

Hereinafter, the present invention will be described in more detail through Examples. These Examples are provided only for more specifically describing the present invention, and it will be obvious to a person with ordinary skill in the art to which the present invention pertains that the scope of the present invention is not limited by these Examples according to the gist of the present invention.

EXAMPLES

Example 1. Preparation of Porous Iron Oxide-Zirconia Catalyst

A polystyrene was manufactured using 10 g of Styrene (Sigma Aldrich, Acs reagent, 99% US) and not using emulsifier. Specifically, 4.685 mL of Styrene was added to 200 mL of distilled water strong agitation and the temperature raised to 80° C., followed by 30 minutes of nitrogen purging. When the state of the solution was sufficiently stabilized to 80° C., 0.47 g of potassium persulfate (KPS, Sigma Aldrich, Acs reagent, 99%, US) was taken into the reactor as initiator, and then the solution was polymerized by stirring it at 200 rpm, 80° C. for 12 hours. By centrifuging the emulsion including the polystyrene of the same size at 8000 rpm for 15 minutes, followed by drying the resultant at room temperature for a day, a spherical polymer template mold arranged in an fcc structure and having the average pore size of 1.1 μm was obtained.

After iron(III) nitrate anhydride and zirconium (IV) oxynitrate hydrate was mixed in molar ratio of 8:1, followed by adding 20 mL of distilled water, the mixture was stirred at room temperature enough, and then injected into the spherical polymer template mold above manufacture. And then, the polymer template mold was dried under the condition of 65° C. for 12 hours. Then, the dried polymer template mold was sintered under the condition of 900° C. for 4 hours to carbonize it and removed, thereby obtaining the porous iron oxide-zirconia composite catalyst having the average pore size of 900 nm.

Example 2. Preparation of Porous Iron Oxide-Zirconia Catalyst

Except that the molar ratio in which iron (III) nitrate anhydride and zirconium (IV) oxynitrate hydrate was 4:1, the porous iron oxide-zirconia composite catalyst was obtained by the same method as the method of the example 1.

Example 3. Preparation of Porous Iron Oxide-Zirconia Catalyst

Except that the molar ratio in which iron (III) nitrate anhydride and zirconium (IV) oxynitrate hydrate was 2:1, the porous iron oxide-zirconia composite catalyst was obtained by the same method as the method of the example 1.

Example 4. Preparation of Porous Iron Oxide-Zirconia Catalyst

Except using 18 mL rather than 4.685 mL of Styrene and 0.21 g rather than 0.47 g of KPS to form spherical polymer template mold having the average size of 200 nm, the porous iron oxide-zirconia composite catalyst having the average pore size of 170 nm was obtained by the same method as that in Example 1.

Experimental Example 1. Electron Microscope Image Analysis

Catalyst particles from the catalysts in the examples were attached onto a carbon tape by using an electron microscope (JEOL, Japan), the carbon tape was coated with gold, and then the catalyst were measured with an SEM at a magnification of ×10,000, and the results thereof are illustrated in FIGS. 1A to 1E.

As can be confirmed from FIG. 1A to 1E, the iron oxide-zirconia composite catalyst prepared in the examples exhibited a porous structure.

Experimental Example 2. Transmission Electron Microscopy (TEM) Analysis 5 mg of the catalyst in the Example 1 was dispersed in 1 ml of a water solvent with ultrasonic waves for about 5 minutes, and then a TEM (manufactured by JEOL, model name JEM-2100F) analysis was performed by loading the catalyst onto a TEM grid, and the result thereof is illustrated in FIG. 2A.

Figure 2A:
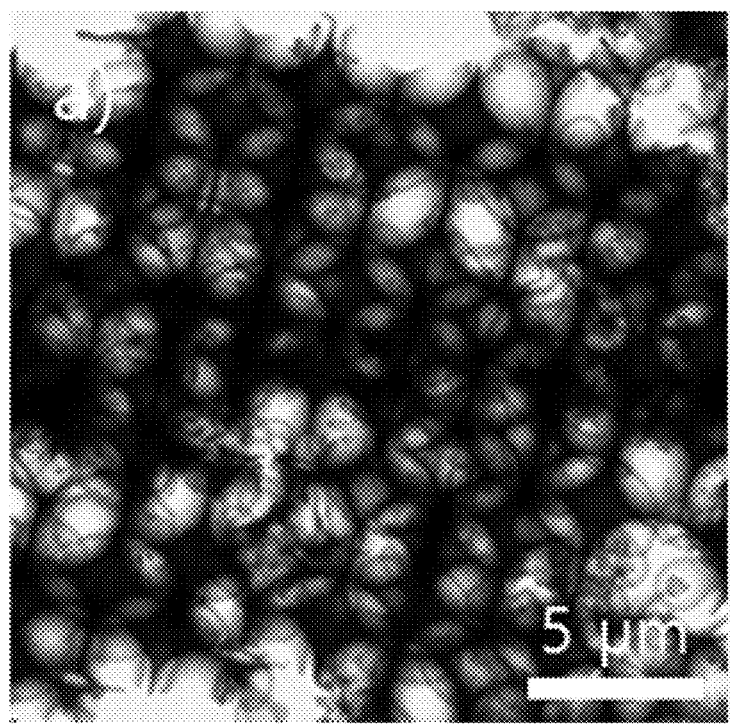
FIG. 2A is a transmission electron microscopy (TEM) image of inverse opal (IO) particles of a porous iron oxide-zirconia composite catalyst produced according to the exemplary embodiment 1 of the present invention.

As can be confirmed from FIG. 2A, a porous structure was uniformly manufactured.

Experimental Example 3. Energy Dispersive Spectroscopy (EDS) Mapping Analysis

Figure 2B:
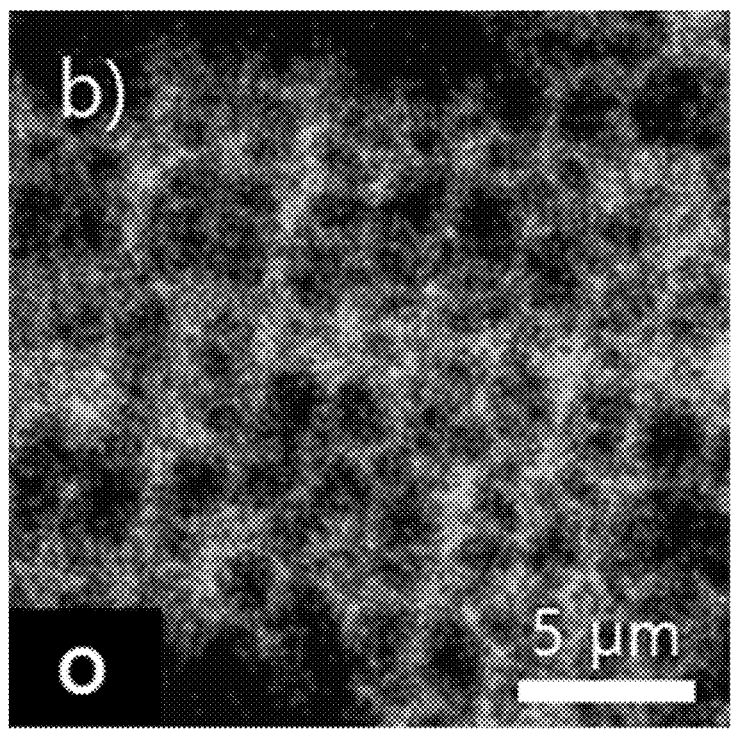
FIG. 2B is an image of an TEM-EDS (energy dispersive spectroscopy) analysis result exhibiting the distribution of oxygen elements for the IO particles of the porous iron oxide-zirconia composite catalyst produced according to an exemplary embodiment 1 of the present invention.
Figure 2C:
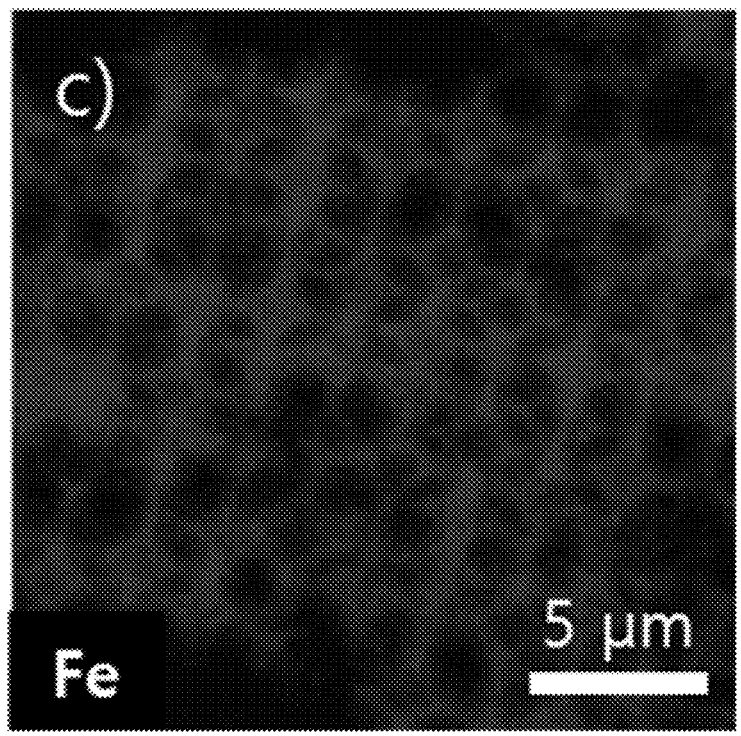
FIG. 2C is an image of an TEM-EDS (energy dispersive spectroscopy) analysis result exhibiting the distribution of iron elements for the IO particles of the porous iron oxide-zirconia composite catalyst produced according to an exemplary embodiment 1 of the present invention.
Figure 2D:
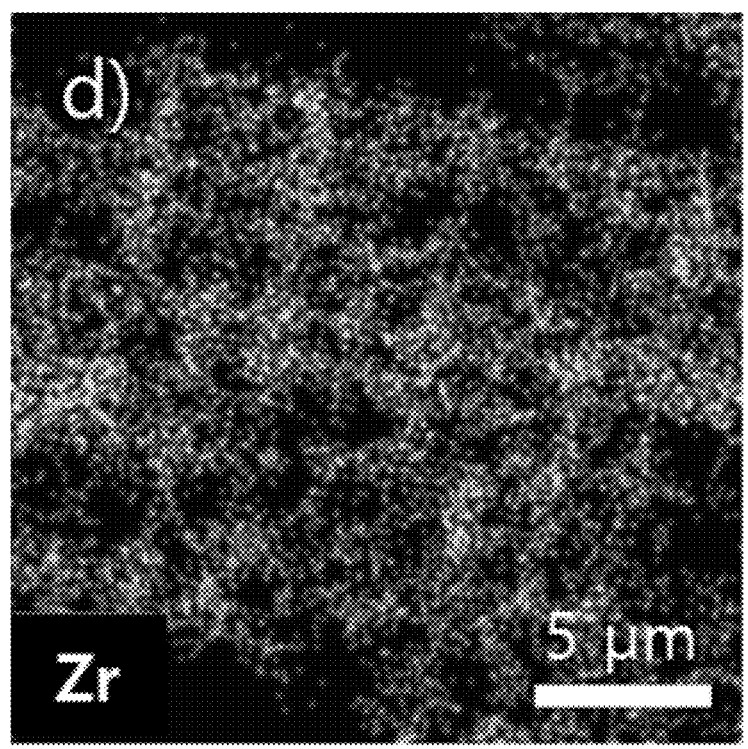
FIG. 2D is an image of an TEM-EDS (energy dispersive spectroscopy) analysis result exhibiting the distribution of zirconium elements for the TO particles of the porous iron oxide-zirconia composite catalyst produced according to an exemplary embodiment 1 of the present invention.

During the TEM analysis, the TEM images were captured, the EDS mapping analyses for iron, zirconium, and oxygen elements were performed at the corresponding positions through the EDS analysis functions, and the results thereof are illustrated in FIGS. 2B to 2D.

As can be confirmed from FIGS. 2B to 2D, iron oxide and zirconia were present in mixture in the catalyst in the Example 1 to 3 and iron and zirconia elements were uniformly distributed along the IO (Inverse Opal) framework.

Experimental Example 4. XRD (X-Ray Diffraction) Analysis

Figure 3:
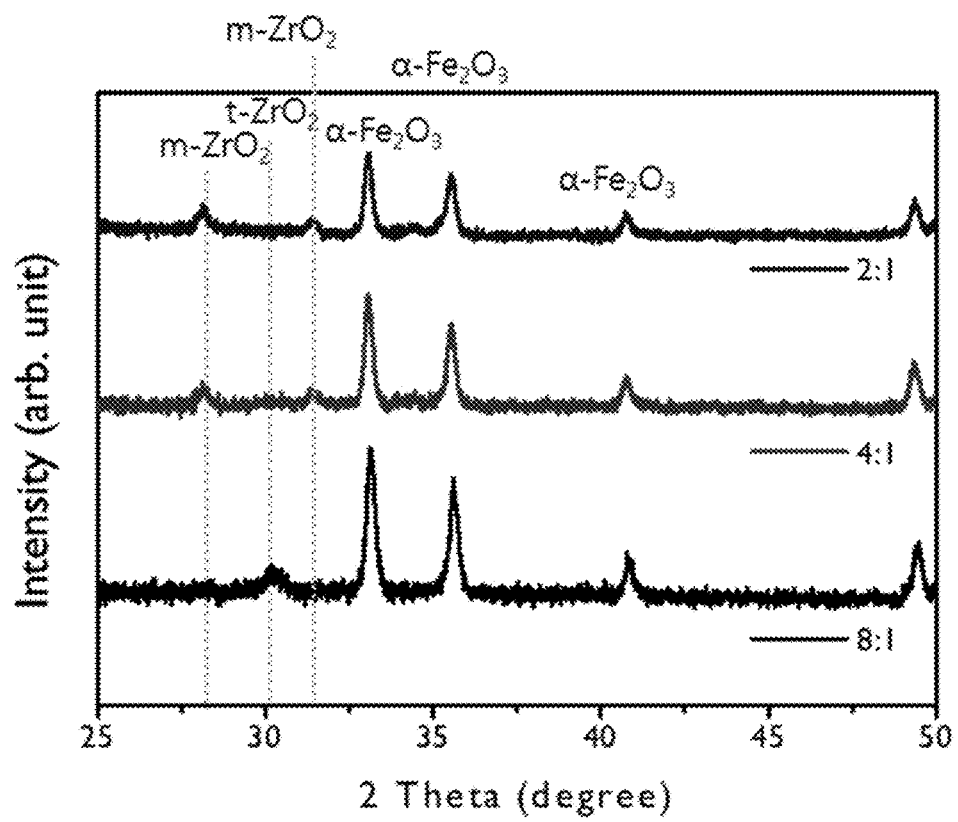
FIG. 3 is a graph showing an XRD (X-ray diffraction) analysis result of the porous iron oxide-zirconia composite catalyst produced according to an exemplary embodiment 1 to 3 of the present invention.

The porous iron oxide-zirconia composite catalyst was applied onto a grid, and then while the grid was irradiated with an X-ray beam, the crystallinity of the corresponding particles was analyzed by measuring the diffraction of the beam while changing the angle of the beam into 2 theta/min, and the results thereof are illustrated in FIG. 3. (Used device manufactured by Rigaku, model name: MINIFLEX)

As can be confirmed from FIG. 3, alpha phase iron oxide peaks at 33.12° (104), 35.63° (110), 40.64° (113) and 49.47° (024), and tetragonal phase zirconia at 30.2° (111) were identified.

Experimental Example 5. XPS (X-Ray Photoelectron Spectroscopy) Analysis

An XPS analysis was performed on a catalyst prepared by mixing iron (III) nitrate anhydride and zirconium (IV) oxynitrate hydrate at a molar ratio of examples 1 to 3 by using an X-ray beam with MXR1 Gun—400 μm 15 kV. Specifically, by using an XPS device manufactured by Thermo Fisher Scientific Inc. (Britain), an X-ray source was monochromated Al Kα (hv=1,486.6 eV), the catalyst were measured at an energy of 15 kV and 100 W by scanning the energy at 0.1 eV, and the results thereof are illustrated in FIGS. 4A and 4B.

Figure 4A:
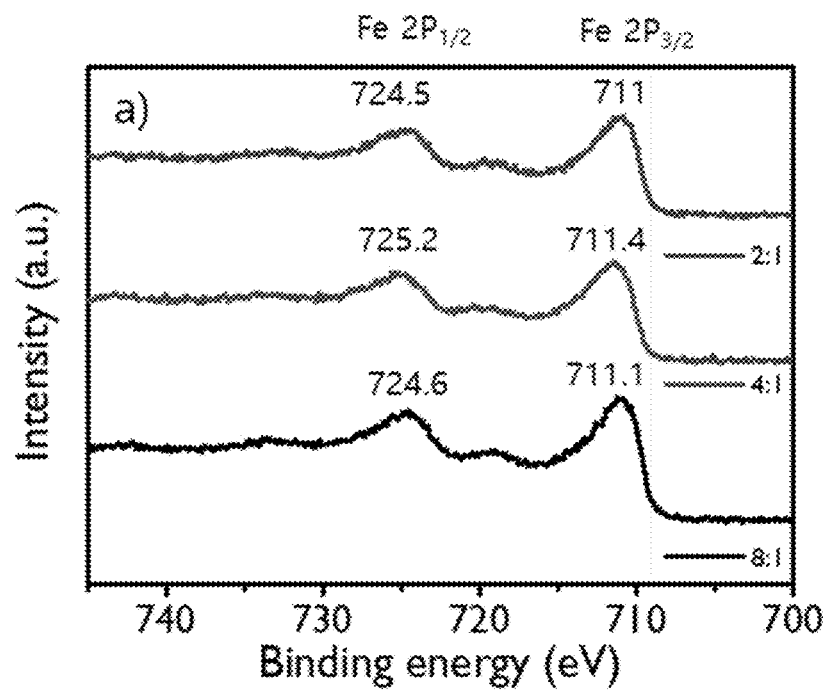
FIG. 4A is a graph showing an XPS (X-ray photoelectron spectroscopy) (Fe 2p) analysis result of the porous iron oxide-zirconia composite catalyst produced according to the exemplary embodiment 1 to 3 of the present invention.
Figure 4B:
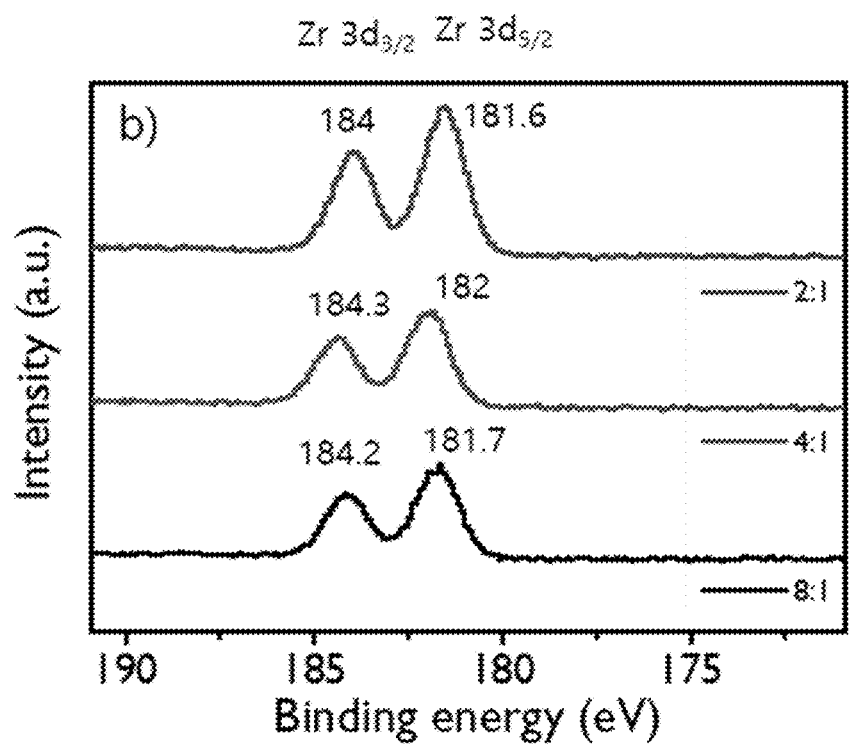
FIG. 4B is a graph showing an XPS (Zr 3d) analysis result of the porous iron oxide-zirconia composite catalyst produced according to the exemplary embodiment 1 to 3 of the present invention.

As can be confirmed from FIGS. 4A and 4B, it was confirmed that the chemical interaction between iron oxide and zirconia was present, and specifically, XPS peak of the BE (binding energy) of Fe 2p 1/2 of the iron oxide appeared markedly around 724.5-725.2 eV, XPS peak of the BE of Fe 2p 3/2 appeared markedly around 711-711.4 eV. The BE XPS peak of the Zr 3d 3/2 of zirconia appeared markedly around 184-184.3 eV, the BE XPS peak of Zr 3d 5/2 of zirconia appeared markedly around 181.6-182 eV. It is determined that the bonding energy results from a chemical interaction instead of a physical interaction.

Experimental Example 6. Electrochemical Evaluation of Cyclic Voltammetry (CV)

After methane and an inert gas were each saturated in a 0.5 M $Na_2CO_3$ solution, a three-electrode electrochemical evaluation was performed in a 15-ml vial.

Figure 5A:
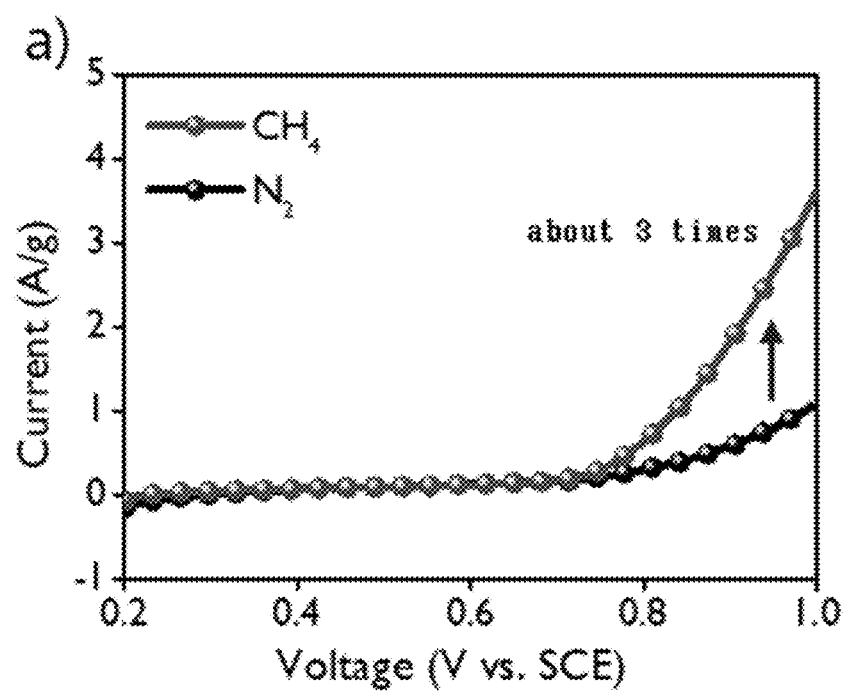
FIG. 5A is a graph showing a cyclic voltammetry analysis result of the porous iron oxide-zirconia composite catalysts produced according to the exemplary embodiment 1 of the present invention with respect to methane saturated solutions.
Figure 5B:
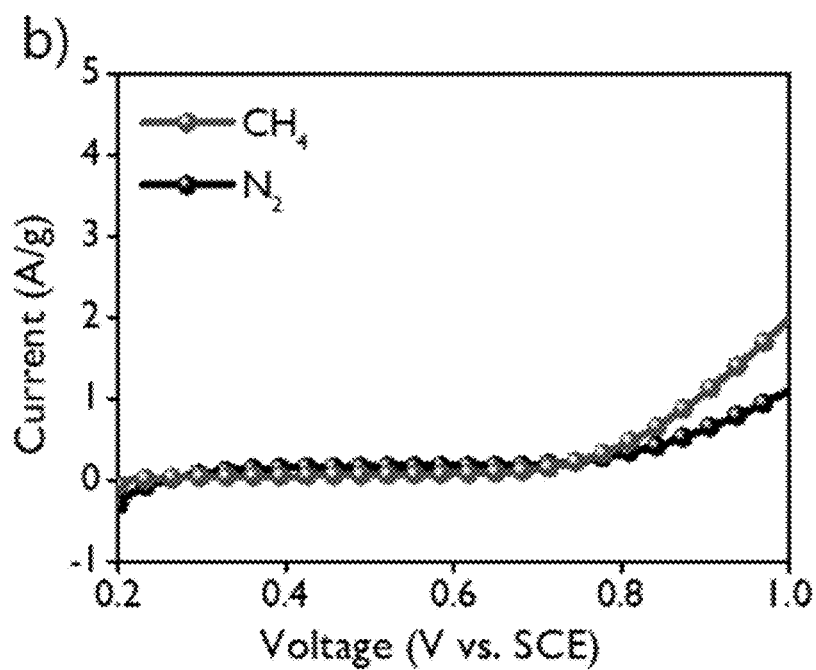
FIG. 5B is a graph showing a cyclic voltammetry analysis result of the porous iron oxide-zirconia composite catalysts produced according to the exemplary embodiment 2 of the present invention with respect to methane saturated solutions.
Figure 5C:
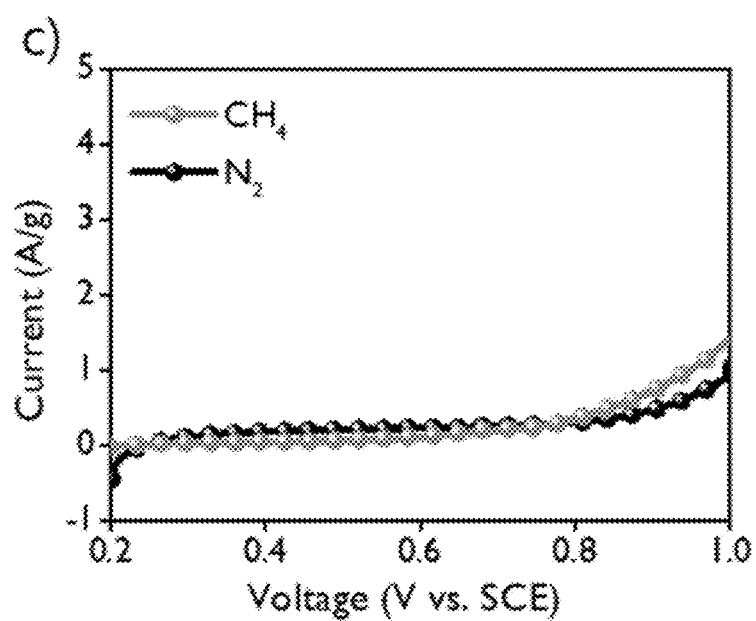
FIG. 5C is a graph showing a cyclic voltammetry analysis result of the porous iron oxide-zirconia composite catalysts produced according to the exemplary embodiment 3 of the present invention with respect to methane saturated solutions.

60 μg of the prepared catalyst of the examples 1 to 3 was loaded onto a glassy carbon electrode, and then a cyclic voltammetry evaluation was performed from 0.2 V to 1.0 V by using the above-mentioned glassy carbon electrode as a working electrode, an SCE electrode as a reference electrode, and Pt as a counter electrode, and the results thereof are illustrated in FIGS. 5A, 5B and 5C.

As can be seen in FIG. 5A, as a result of CV of iron oxide in a $CO_3^{2-}$ electrolyte solution, methane activation was confirmed at 0.8 V or more. $CH_4$-saturated condition led to the current about three times that obtained under Ar-saturated condition.

As can be confirmed from FIG. 5B, as a result of CV of iron oxide in a $CO_3^{2-}$ electrolyte solution, slight methane activation could be identified at 0.8 V or more. About 2 times increased current could be identified under $CH_4$-saturated condition compared to Ar-saturated condition, in the above-mentioned reactions.

As can be confirmed from FIG. 5C, little methane activation could be identified at 0.8 V or more. About 1.4 times increased current could be identified under $CH_4$-saturated condition compared to Ar-saturated condition, in the aforementioned reactions.

Experimental Example 7. Qualitative Analysis of the Product of Methane Oxidation Reaction In order to allow methane in a liquid phase to react, a solution was saturated by supplying methane with a purity of 99.999% to a $Na_2CO_3$ solution at a concentration of 0.5 M for 1 hour, and an empty space of the reactor was fully filled with methane. Next, to both sides of the reactor, a Pt electrode as a cathode was connected and a carbon paper, as an anode, in which the catalyst was uniformly loaded was connected. The catalyst was dispersed in water, placed onto the carbon paper, and then dried, and the catalyst was loaded onto the carbon paper electrode by fixing the catalyst using a binder, and the reactor was made hermetically sealed and isolated from the outside.

Figure 6:
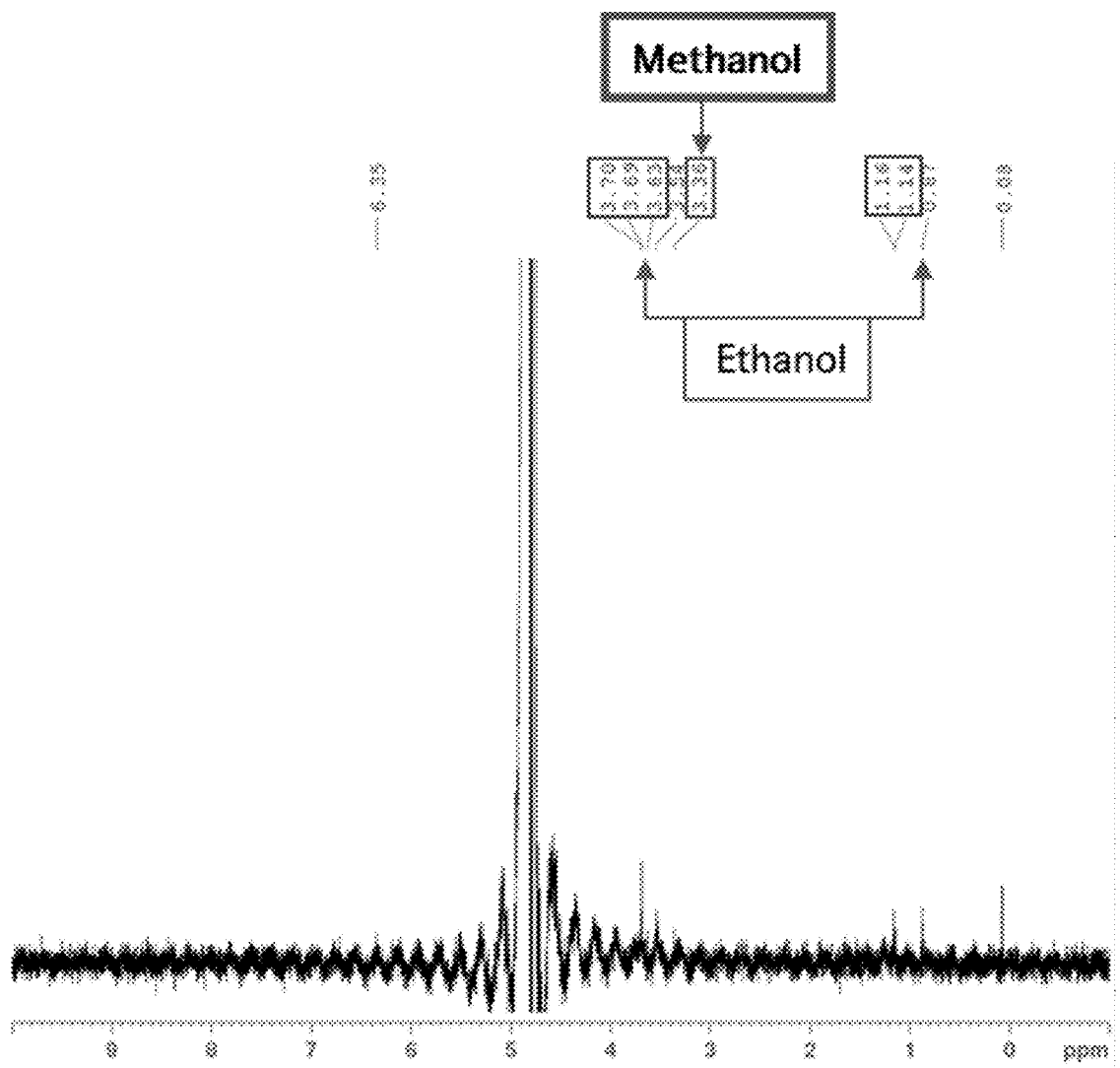
FIG. 6 is an NMR (Nuclear Magnetic Resonance Spectroscopy) spectrum of the product of the methane oxidation reaction using the porous iron oxide-zirconia composite catalyst produced according to the exemplary embodiment 1 of the present invention.

Using the porous iron oxide-zirconia composite catalyst prepared from Example 1, methane oxidation reaction was carried out for 12 hours under room temperature and normal pressure condition to obtain a product, and then the product was analyzed by NMR, with result thereof illustrated in FIG. 6.

Generally, the $^1$H-NMR peaks of methanol appear around 3.3~3.5 ppm, while the peak was detected in this reaction, appeared at 3.36 ppm. The ethanol peaks generally appear around 1.1~1.2 ppm, and 3.6~3.7 ppm, while the peaks was detected in this reaction, were detected at 3.63, 3.69, 3.7 ppm and 1.14, 1.16 ppm.

Compared to the major products, all minor products were identified by negligible amount.

Experimental Example 8. Quantitative Analysis of the Product of Methane Oxidation Reaction The products of 12 hours of methane oxidation reaction under 1.5 V with the porous iron oxide-zirconia composite catalyst prepared in the examples 1 to 3 were analyzed by GC/MS, and the results thereof were illustrated in the FIG. 7 and the Table 1.

TABLE 1

|  | methanol | ethanol | 1-propanol | formaldehyde |
|---|---|---|---|---|
| example 1 | 6.03 | 0.43 | 1.1 | 0.02 |
| example 2 | 4.18 | 0.52 | 1.59 | 0.008 |
| example 3 | 2.45 | 0.76 | 0.08 | 0.007 | product amount(mg/L)

Figure 7:
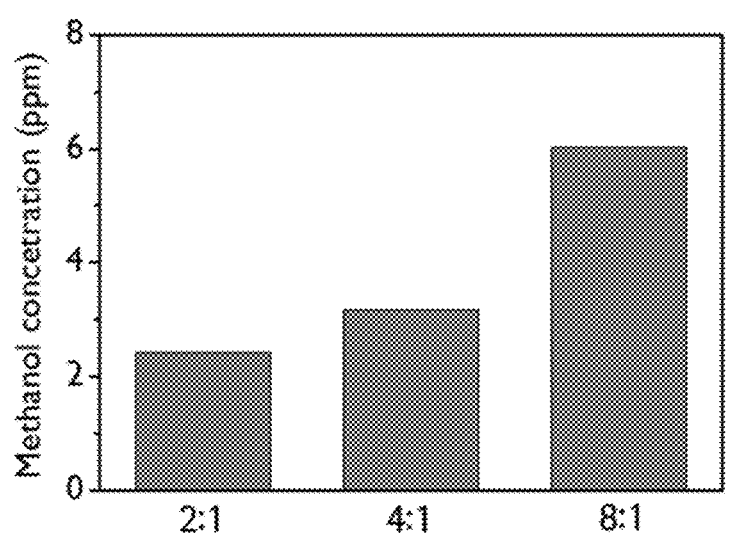
FIG. 7 is a graph showing results of analyzing a concentration of methanol produced according to the time for a methane oxidation reaction using the porous iron oxide-zirconia composite catalyst produced according to the exemplary embodiment 1 to 3 of the present invention.

FIG. 7 is a graph showing the analyzed results of the methanol production concentration according to the methane oxidation reaction time, in which the porous iron oxide-zirconia composite catalyst prepared from the examples 1 to 3 of the present invention.

As can be confirmed in the FIG. 7 and the table 1, methanol (MeOH), ethanol (EtOH), 1-propanol (1-PrOH), formaldehyde, and the like were detected as methane oxidation reaction products, and methanol was detected as a main product at high ratio.

That which is claimed is:

1. A method for preparing a porous iron oxide-zirconia composite catalyst, the method including:
   impregnating a polymer template mold with a precursor mixture of an iron oxide precursor and a zirconia precursor, wherein the iron oxide precursor and the zirconia precursor are provided in the mixture at a molar ratio of 8:1;
   drying the polymer template mold impregnated with the precursor mixture to form a dried polymer template mold; and
   sintering the dried polymer template mold at a temperature of from 700 to 1100° C.,
   wherein the porous iron oxide-zirconia composite catalyst comprises tetragonal phase zirconia and alpha phase iron oxide.

2. The method of claim 1,
   wherein the iron oxide precursor is one or more selected from the group consisting of iron (III) nitrate, iron (III) chlorate, and iron (III) sulfate.

3. The method of claim 1,
   wherein the zirconia precursor is one or more selected from the group consisting of zirconium oxynitrate, zirconium nitrate, and zirconium sulfate.

4. The method of claim 1,
   wherein the polymer template mold includes a spherical polymer arranged in a face centered cubic (fcc) structure.

5. The method of claim 1,
   wherein the polymer template mold is manufactured by a method including emulsion polymerization of monomers, followed by a drying step.

6. The method of claim 1,
   wherein the polymer template mold includes one or more polymers selected from the group consisting of poly (methyl methacrylate) [PMMA], poly(butyl methacrylate) [PBMA], poly(methyl methacrylate)(butyl methacrylate), poly(hydroxyethyl methacrylate) [PHEMA], and polystyrene.

* * * * *